(12) United States Patent
DeRidder et al.

(10) Patent No.: US 8,454,621 B2
(45) Date of Patent: Jun. 4, 2013

(54) INSTRUMENTS AND METHODS FOR SPINAL IMPLANT REVISION

(75) Inventors: Steven D. DeRidder, Bartlett, TN (US); Brian Robert Thoren, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1371 days.

(21) Appl. No.: 11/523,408

(22) Filed: Sep. 19, 2006

(65) Prior Publication Data

US 2008/0097454 A1   Apr. 24, 2008

(51) Int. Cl.
*A61B 17/88* (2006.01)
*A61B 17/92* (2006.01)
*A61B 17/58* (2006.01)
*A61F 2/44* (2006.01)

(52) U.S. Cl.
USPC ........................................ 606/99; 623/17.16

(58) Field of Classification Search
USPC . 606/246, 279, 86 R, 99, 90, 100; 623/17.11, 623/17.16
See application file for complete search history.

(56) References Cited

U.S. PATENT DOCUMENTS

| | | | | |
|---|---|---|---|---|
| 4,927,425 A * | 5/1990 | Lozier | | 606/99 |
| 5,180,388 A | 1/1993 | DiCarlo | | |
| 5,466,243 A | 11/1995 | Schmieding et al. | | |
| 5,531,785 A * | 7/1996 | Love et al. | | 623/2.11 |
| 5,782,830 A * | 7/1998 | Farris | | 606/99 |
| 5,951,564 A * | 9/1999 | Schroder et al. | | 606/100 |
| 6,113,602 A * | 9/2000 | Sand | | 606/86 A |
| 6,264,657 B1 | 7/2001 | Urbahns et al. | | |
| 6,478,800 B1 * | 11/2002 | Fraser et al. | | 606/99 |
| 6,478,801 B1 | 11/2002 | Ralph et al. | | |
| 6,562,047 B2 | 5/2003 | Ralph et al. | | |
| 6,712,819 B2 | 3/2004 | Zucherman et al. | | |
| 6,755,841 B2 * | 6/2004 | Fraser et al. | | 606/99 |
| 6,805,716 B2 | 10/2004 | Ralph et al. | | |
| 6,887,248 B2 * | 5/2005 | McKinley et al. | | 606/99 |
| 6,923,814 B1 * | 8/2005 | Hildebrand et al. | | 606/99 |
| 6,926,728 B2 | 8/2005 | Zucherman et al. | | |
| 7,060,073 B2 * | 6/2006 | Frey et al. | | 606/85 |
| 7,235,082 B2 * | 6/2007 | Bartish et al. | | 606/99 |
| 7,244,258 B2 * | 7/2007 | Burkus et al. | | 606/90 |
| 7,294,134 B2 * | 11/2007 | Weber | | 606/99 |
| 7,320,688 B2 * | 1/2008 | Foley et al. | | 606/99 |
| 7,320,689 B2 * | 1/2008 | Keller | | 606/99 |
| 2001/0010001 A1 | 7/2001 | Michelson | | |
| 2001/0020170 A1 * | 9/2001 | Zucherman et al. | | 606/99 |
| 2001/0047207 A1 * | 11/2001 | Michelson | | 623/17.11 |
| 2002/0045904 A1 * | 4/2002 | Fuss et al. | | 606/99 |
| 2002/0058950 A1 * | 5/2002 | Winterbottom et al. | | 606/99 |

(Continued)

FOREIGN PATENT DOCUMENTS

DE   202004014120 U1   12/2004
WO   WO02/091909 A2   11/2002

*Primary Examiner* — Michael T Schaper

(57) ABSTRACT

Instruments and methods are provided for re-positioning and extracting spinal implants in a space between vertebrae. The instruments can include rotator instruments, hook instruments, and extractor instruments engageable to the implant. A method for manipulating a spinal implant in a space between vertebrae includes positioning a spinal implant in the space between vertebrae; engaging the spinal implant with a hook member at a distal end of a hook instrument; pulling the spinal implant toward an opening into the space between the vertebrae; grasping the spinal implant with an engaging assembly of an extractor instrument; and removing the spinal implant from the space with the extractor instrument.

13 Claims, 9 Drawing Sheets

U.S. PATENT DOCUMENTS

| | | | |
|---|---|---|---|
| 2002/0165550 A1* | 11/2002 | Frey et al. | 606/85 |
| 2002/0165612 A1* | 11/2002 | Gerber et al. | 623/17.11 |
| 2002/0177897 A1* | 11/2002 | Michelson | 623/17.11 |
| 2003/0014057 A1* | 1/2003 | Ralph et al. | 606/99 |
| 2003/0028197 A1 | 2/2003 | Hanson et al. | |
| 2003/0149438 A1* | 8/2003 | Nichols et al. | 606/99 |
| 2003/0216744 A1* | 11/2003 | Longhini et al. | 606/99 |
| 2003/0229358 A1* | 12/2003 | Errico et al. | 606/99 |
| 2004/0024408 A1* | 2/2004 | Burkus et al. | 606/90 |
| 2004/0030346 A1* | 2/2004 | Frey et al. | 606/99 |
| 2004/0098129 A1 | 5/2004 | Lin | |
| 2004/0148028 A1 | 7/2004 | Ferree et al. | |
| 2004/0167538 A1* | 8/2004 | Gerber et al. | 606/99 |
| 2004/0193213 A1 | 9/2004 | Aranyi et al. | |
| 2004/0199168 A1* | 10/2004 | Bertagnoli et al. | 606/99 |
| 2004/0236370 A1* | 11/2004 | Ralph et al. | 606/207 |
| 2004/0254583 A1* | 12/2004 | McKay et al. | 606/99 |
| 2004/0260338 A1 | 12/2004 | Kupferschmid et al. | |
| 2004/0267164 A1 | 12/2004 | Rhodes et al. | |
| 2005/0027360 A1* | 2/2005 | Webb et al. | 623/17.11 |
| 2005/0038445 A1 | 2/2005 | Errico et al. | |
| 2005/0049623 A1 | 3/2005 | Moore et al. | |
| 2005/0055095 A1* | 3/2005 | Errico et al. | 623/17.11 |
| 2005/0096745 A1* | 5/2005 | Andre et al. | 623/17.11 |
| 2005/0119665 A1* | 6/2005 | Keller | 606/99 |
| 2005/0119753 A1* | 6/2005 | McGahan et al. | 623/17.16 |
| 2005/0131419 A1* | 6/2005 | McCord et al. | 606/99 |
| 2005/0131540 A1* | 6/2005 | Trieu | 623/17.11 |
| 2005/0149048 A1* | 7/2005 | Leport et al. | 606/99 |
| 2005/0165408 A1* | 7/2005 | Puno et al. | 606/99 |
| 2005/0203538 A1* | 9/2005 | Lo et al. | 606/99 |
| 2005/0288788 A1* | 12/2005 | Dougherty-Shah | 623/17.11 |
| 2006/0129238 A1 | 6/2006 | Paltzer | |
| 2006/0212120 A1 | 9/2006 | McGahan et al. | |
| 2008/0097435 A1* | 4/2008 | DeRidder et al. | 606/61 |

* cited by examiner

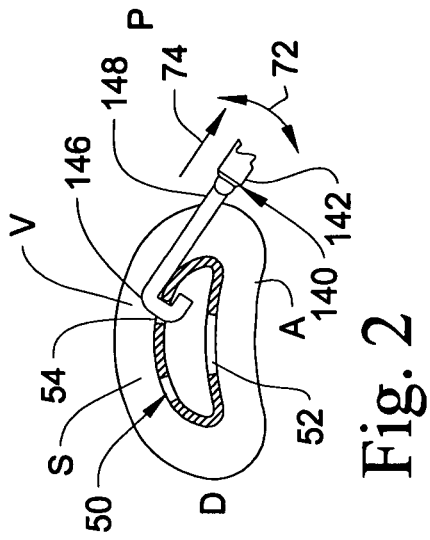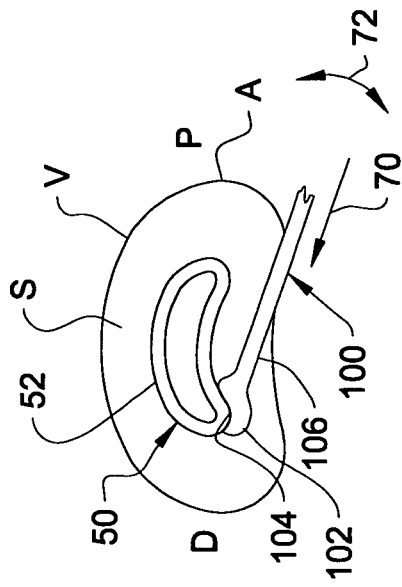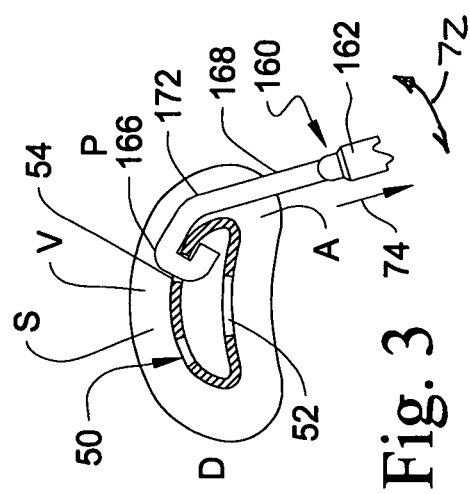

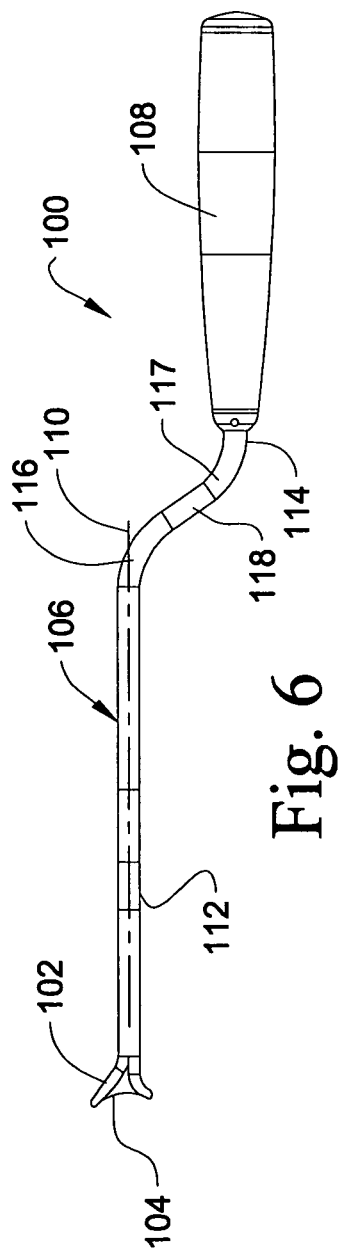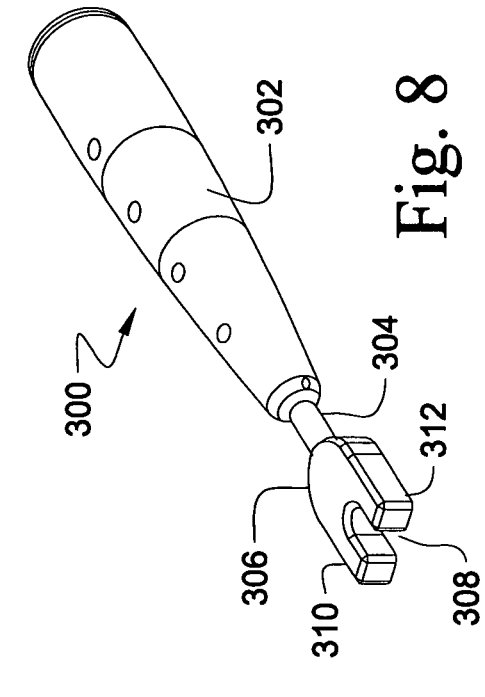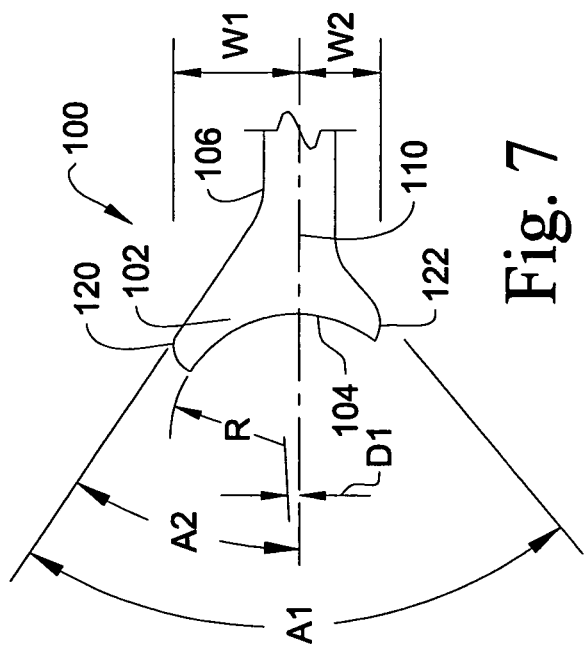

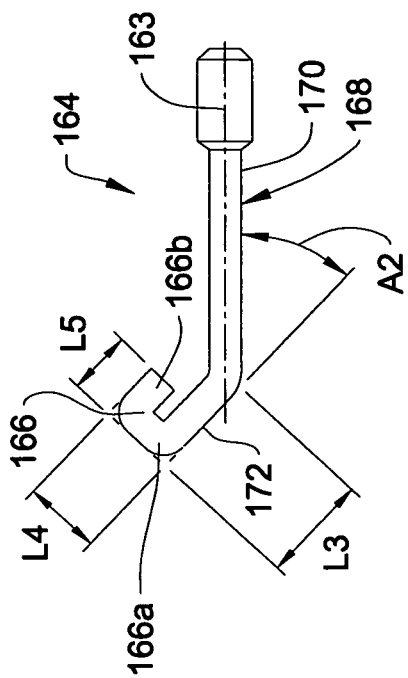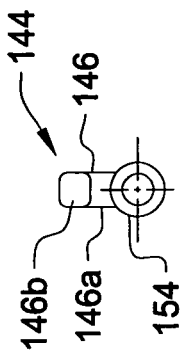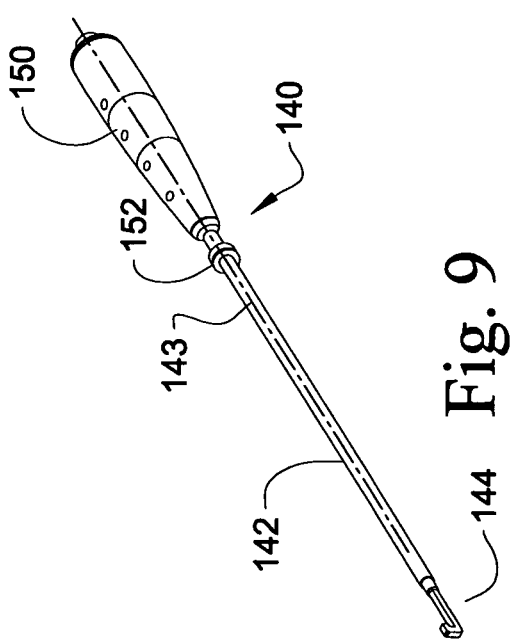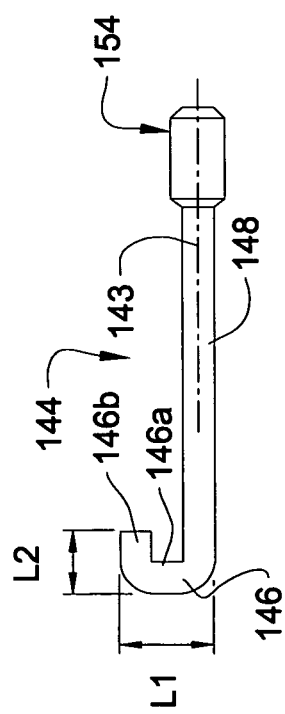
Fig. 12
Fig. 11
Fig. 9
Fig. 10

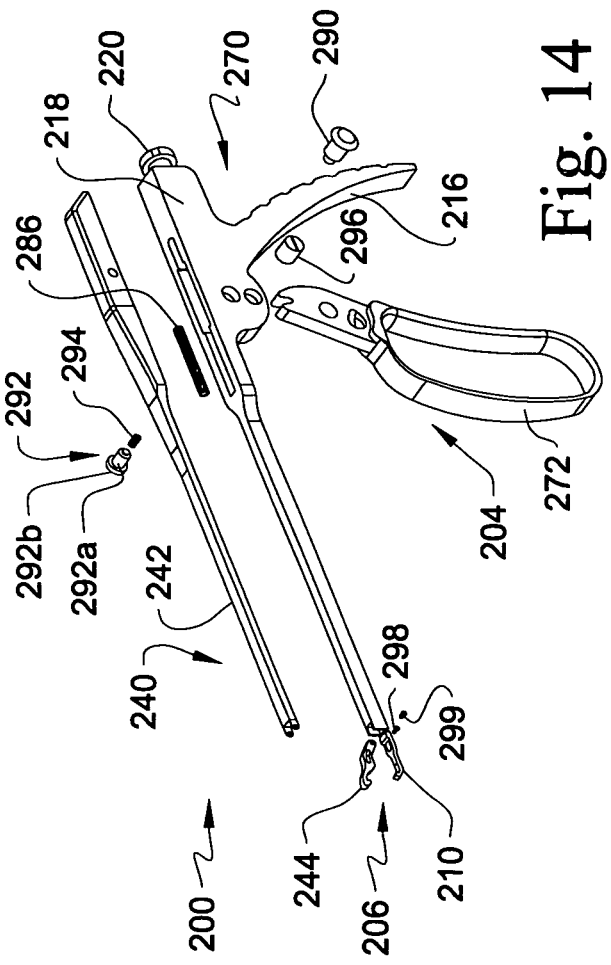
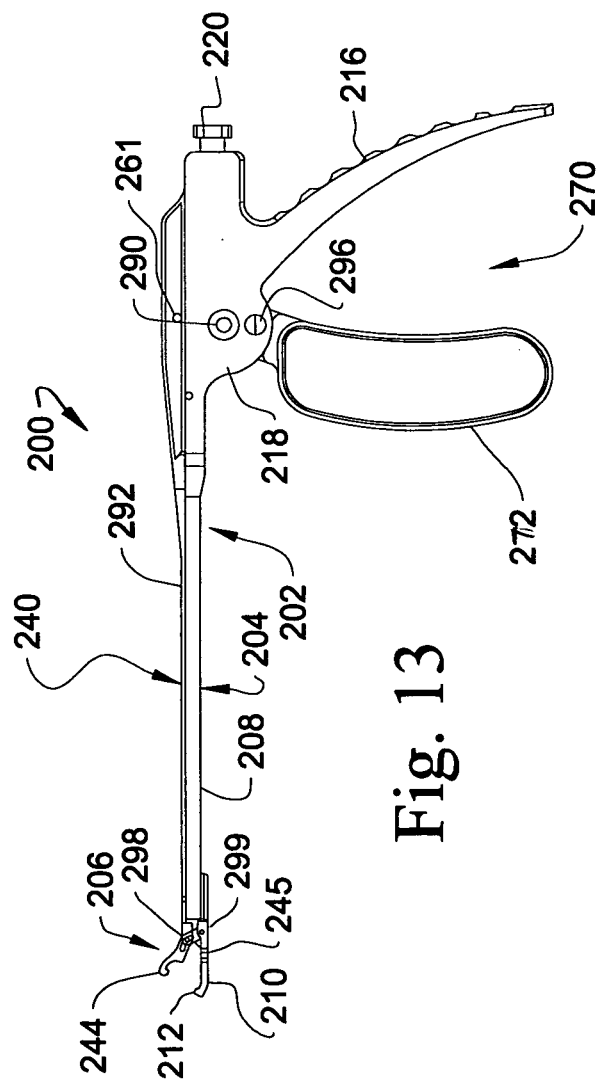
Fig. 14
Fig. 13

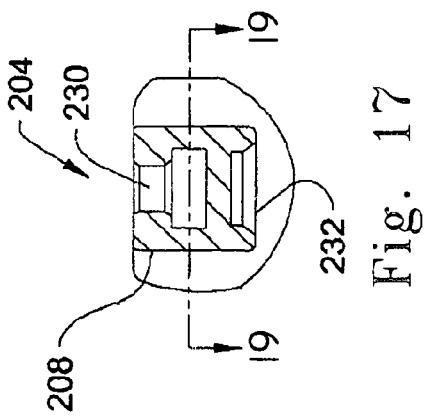
Fig. 17
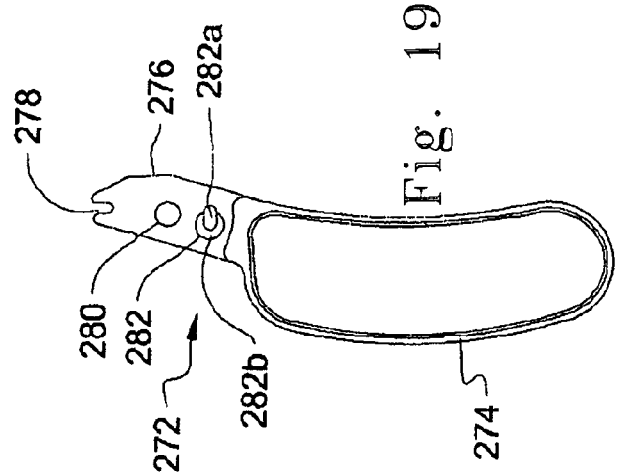
Fig. 19
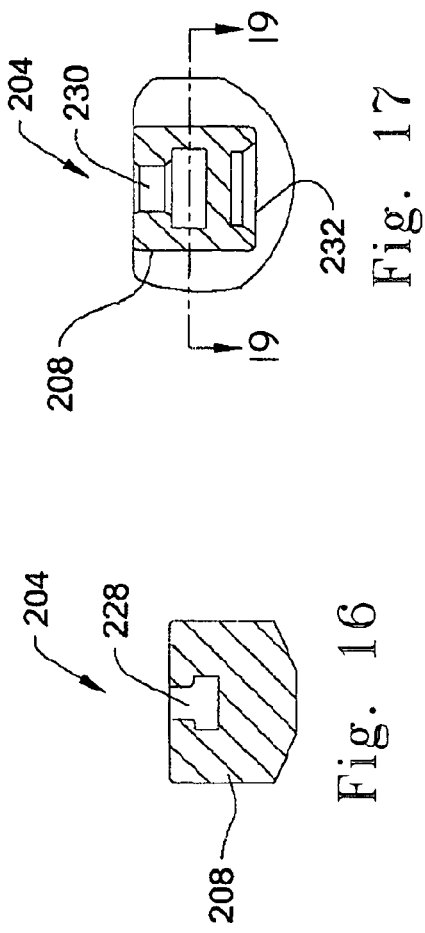
Fig. 16
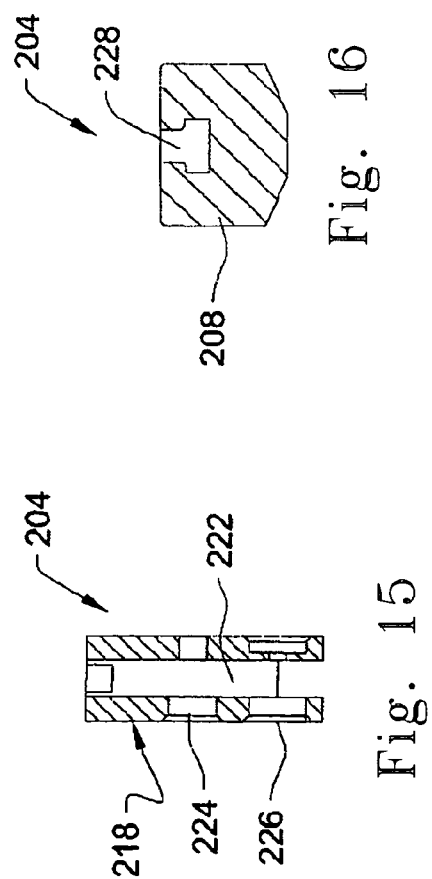
Fig. 15
Fig. 18

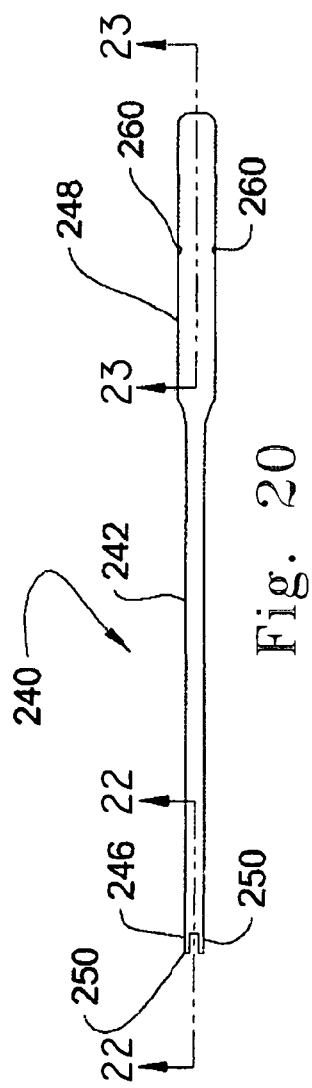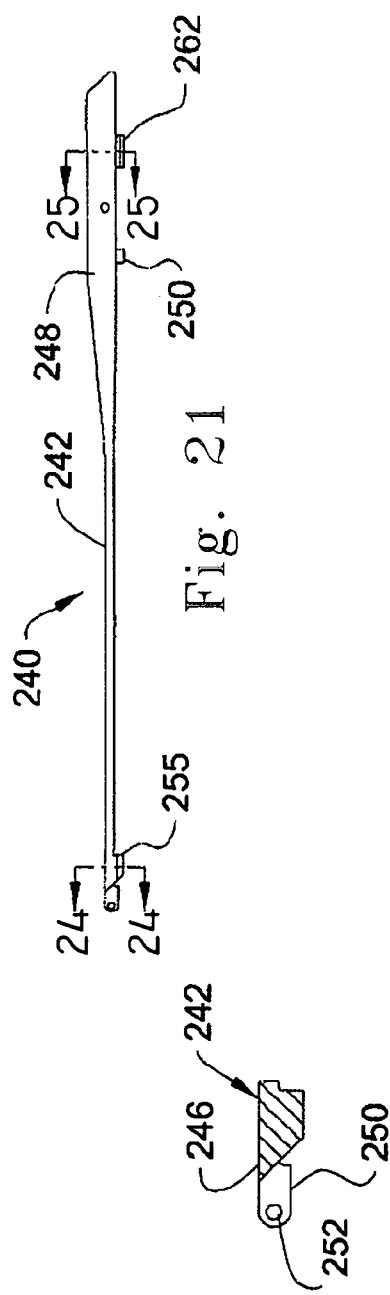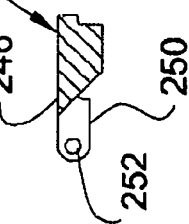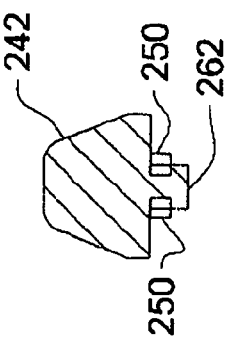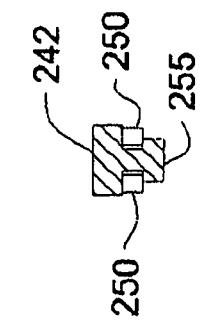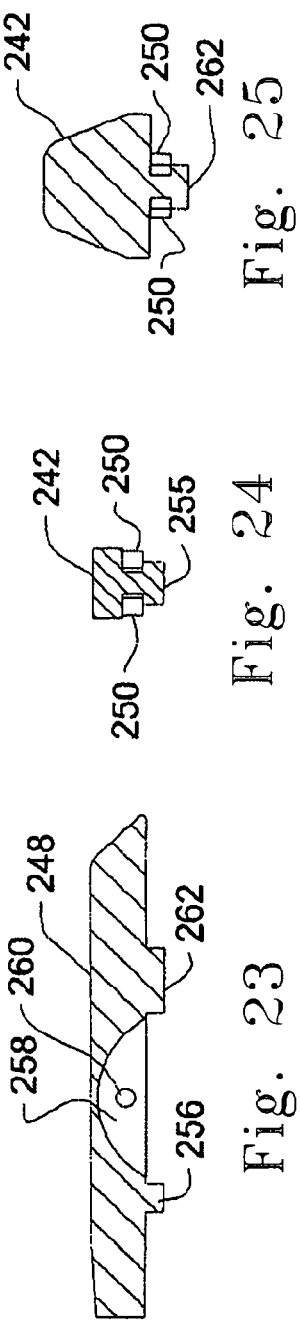

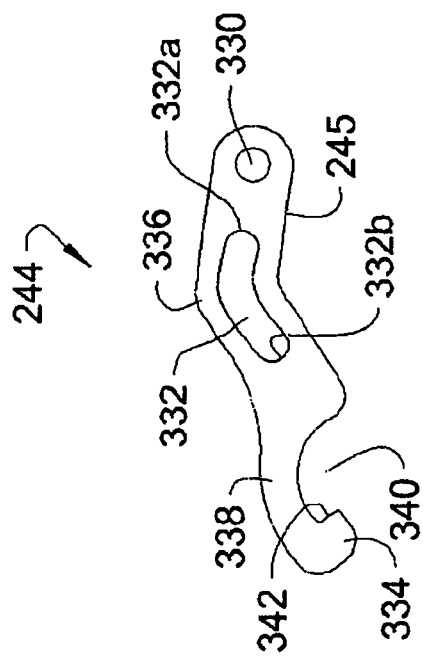
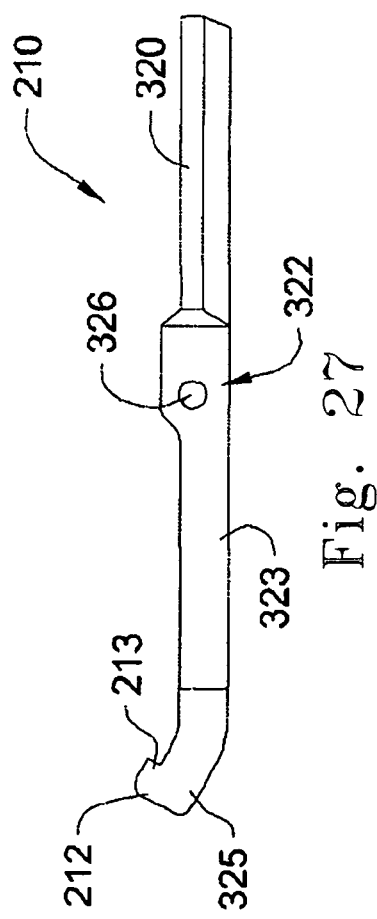
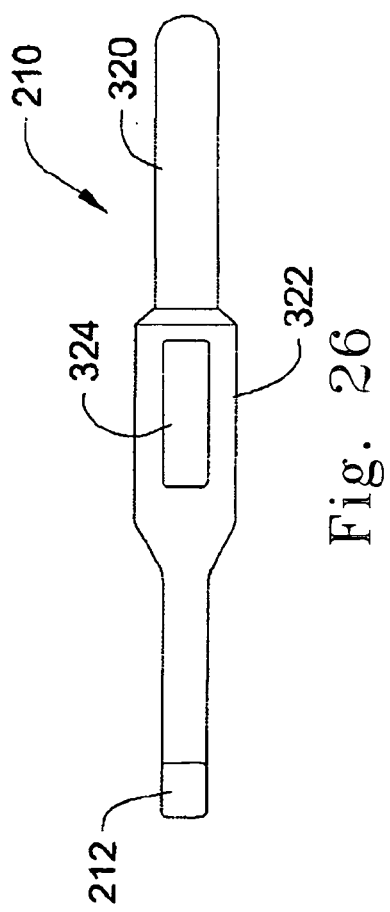

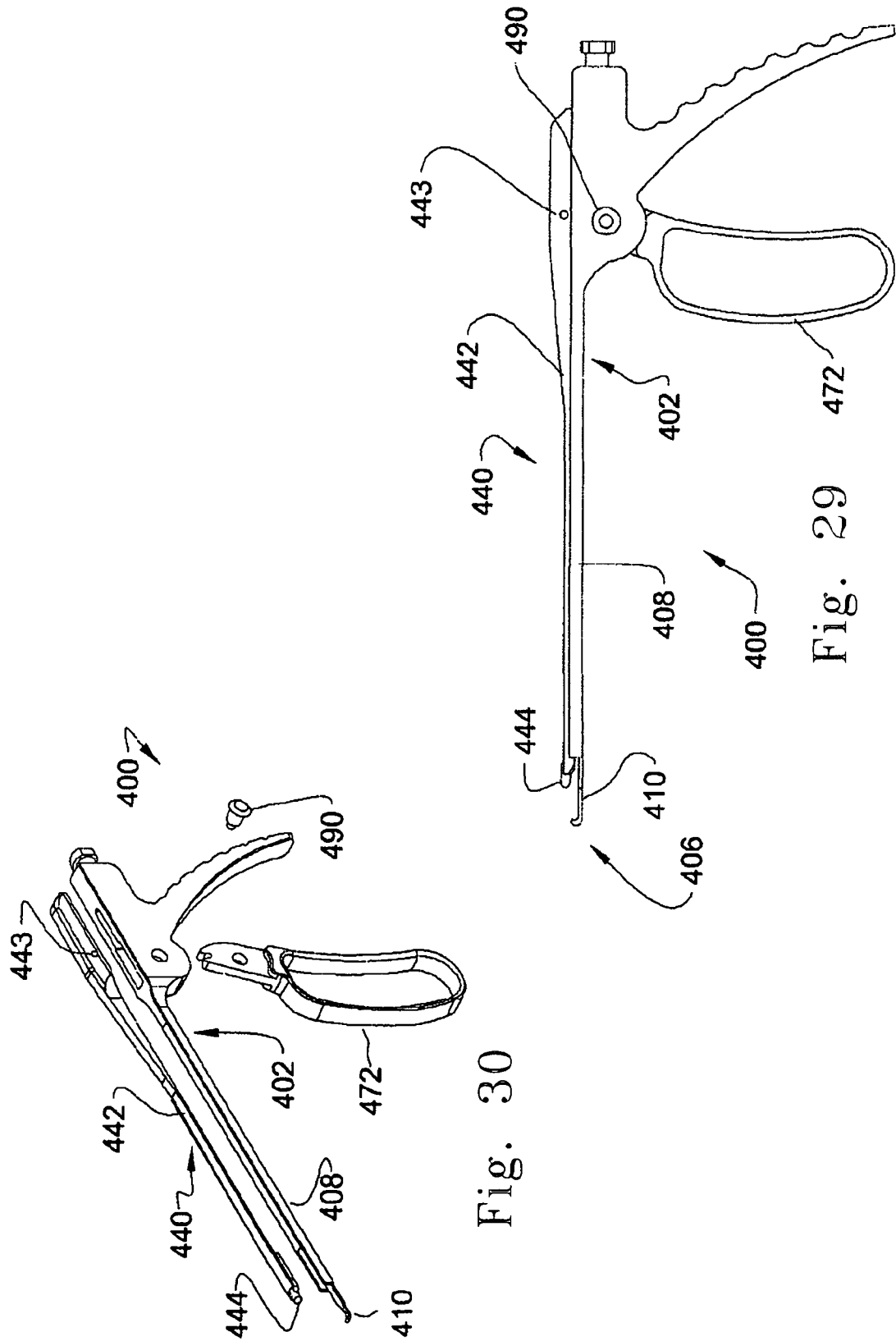

INSTRUMENTS AND METHODS FOR SPINAL IMPLANT REVISION

BACKGROUND

Normal intervertebral discs between endplates of adjacent vertebrae distribute forces between the vertebrae and cushion vertebral bodies. The spinal discs may be displaced or damaged due to trauma, disease or aging. A herniated or ruptured annulus fibrosis may result in nerve damage, pain, numbness, muscle weakness, and even paralysis. Furthermore, as a result of the normal aging processes, discs dehydrate and harden, thereby reducing the disc space height and producing instability of the spine and decreased mobility. Most surgical corrections of a disc space include a discectomy, which can be followed by restoration of normal disc space height and bony fusion of the adjacent vertebrae to maintain the disc space height.

Other procedures can involve removal of one or more vertebral bodies as a result of trauma, disease or other condition. An implant can be positioned between intact vertebrae to provide support until fusion of the affected spinal column segment is attained.

Access to a damaged disc space or to a corpectomy location may be accomplished from several approaches to the spine. One approach is to gain access to the anterior portion of the spine through a patient's abdomen. A posterior or lateral approach may also be utilized. Postero-lateral, antero-lateral and oblique approaches to the spinal column have also been employed to insert implants. Whatever the approach, there may be a need to re-position and/or extract implants after positioning in the spinal disc space or corpectomy location. There remains a need for improved instruments and techniques for use in any approach that facilitate revision of spinal implants in a space between vertebrae.

SUMMARY

There are provided instruments and methods useful for implant re-positioning and extraction from any approach to the spine. Such implants can be employed in disc replacement and/or vertebral body replacement type procedures. The instruments can be provided in a kit to provide the surgeon a variety of instrument options during the procedure.

In one aspect, an assembly for spinal implant revision includes a rotator instrument with an elongate shaft extending along a longitudinal axis, a proximal handle extending from a proximal end of the shaft, and a distal end member at a distal end of the shaft. The distal end member includes a first foot including a first width extending from the longitudinal axis and a second foot including a second width less than the first width extending from the longitudinal axis in a direction opposite the first foot. The distal end member includes a concave distal end wall extending along the first and second feet. The assembly also includes an implant sized and shaped for positioning in a space between vertebrae that includes a wall and at least a portion of the wall has a convex shape that corresponds to a shape of the concave distal end wall.

In another aspect, an assembly for spinal implant revision includes an elongate shaft extending along a longitudinal axis, a proximal handle extending from a proximal end of the shaft, and a distal hook member extending distally from the shaft. The hook member includes an elongate arm extending along the longitudinal axis and a hooked end at a distal end of the arm. The assembly also includes an implant sized and shaped for positioning in a space between vertebrae. The implant includes a receptacle and the hooked end is positioned in the receptacle in engagement with the implant.

In a further aspect, an instrument for engaging a spinal implant includes a shaft assembly, an actuator assembly at a proximal end of the shaft assembly, and an engaging assembly at a distal end of the shaft assembly. The engaging assembly includes a support member fixedly coupled with the shaft assembly and extending distally therefrom and a clamping member coupled with at least one of the shaft assembly and the support member. The actuator assembly is operably linked to the clamping member with the shaft assembly. The clamping member is movable toward the support member with actuation of the actuator assembly to a clamping position for clampingly engaging the implant between the support member and the clamping member. The support member includes an elongated body with a linear proximal section and a distal section angled relative to the proximal section. The distal section includes a flange at a distal end thereof forming a proximally oriented lip extending toward the clamping member and positionable in engagement with the implant.

In another aspect, a kit for repositioning and extracting spinal implants includes a spinal implant, a rotator instrument, at least one hook instrument and at least one extractor instrument. The rotator instrument includes a shaft extending along a longitudinal axis, a proximal handle and a distal end member. The distal end member includes a distal end wall with a shape to conform to a portion of a wall of the implant.

The hook instrument includes a shaft extending along a longitudinal axis between a proximal handle and a distal hook member configured to engage the implant in a receptacle of the implant. The extractor instrument includes a shaft assembly operably linking a proximal actuator assembly and a distal engaging assembly. The distal engaging assembly is operable with the actuator assembly to clampingly engage the implant.

According to one aspect, a method for manipulating a spinal implant in a space between vertebrae comprises: positioning a spinal implant in the space between vertebrae; engaging the spinal implant with a hook member at a distal end of a hook instrument; pulling the spinal implant toward an opening into the space between the vertebrae; grasping the spinal implant with an engaging assembly of an extractor instrument; and removing the spinal implant from the space with the extractor instrument.

These and other aspects will also be apparent from the following description and the drawings.

BRIEF DESCRIPTION OF THE DRAWINGS

FIG. 1 is a plan view of vertebral space with an implant and a distal portion of a rotator instrument.

FIG. 2 is a plan view of a vertebral space with an implant and a distal portion of a hook instrument.

FIG. 3 is a plan view of a vertebral space with an implant and a distal portion of another embodiment hook instrument.

FIG. 6 is a plan view of a rotator instrument.

FIG. 7 is a plan view of a distal end portion of the rotator instrument of FIG. 6.

FIG. 8 is a perspective view of an adjustment instrument.

FIG. 9 is a perspective view of a hook instrument.

FIG. 10 is an elevation view of a distal hook member of the hook instrument of FIG. 9.

FIG. 11 is an end view of the hook member of FIG. 10.

FIG. 12 is a side view of another embodiment hook member.

FIG. 13 is an elevation view of an extractor instrument.

FIG. 14 is an exploded perspective view of the extractor instrument of FIG. 13.

FIG. 15 is a section view of the mounting assembly of the extractor instrument.

FIG. 16 is a section view of the mounting assembly.

FIG. 17 is a section view of the mounting assembly.

FIG. 18 is a section view along line 18-18 of FIG. 17.

FIG. 19 is an elevation view of a trigger of the extractor instrument of FIG. 13.

FIG. 20 is a top plan view of a rail member of the extractor instrument of FIG. 13.

FIG. 21 is an elevation view of the rail member of FIG. 20.

FIG. 22 is a section view along line 22-22 of FIG. 20.

FIG. 23 is a section view along line 23-23 of FIG. 20.

FIG. 24 is a section view along line 24-24 of FIG. 21.

FIG. 25 is a section view along line 25-25 of FIG. 21.

FIG. 26 is a top plan view of a support member of the engaging assembly of the extractor instrument of FIG. 13.

FIG. 27 is an elevation view of the support member of FIG. 26.

FIG. 28 is an elevation view of a clamping member of the engaging assembly of the extractor instrument of FIG. 13.

FIG. 29 is an elevation view of another embodiment extractor instrument.

FIG. 30 is an exploded perspective view of the extractor instrument of FIG. 29.

DETAILED DESCRIPTION OF THE ILLUSTRATED EMBODIMENTS

Figure 4:
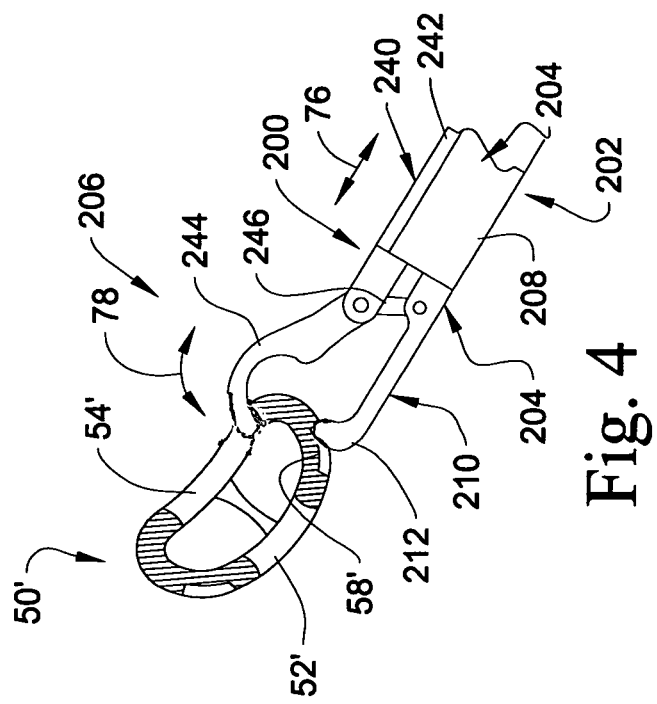
FIG. 4 is a plan view of an implant with a distal portion of an extractor instrument engaged thereto.

For the purposes of promoting an understanding of the principles of the present invention, reference will now be made to the embodiments illustrated in the drawings, and specific language will be used to describe the same. It will nevertheless be understood that no limitation of the scope of the invention is intended thereby. Any alterations and further modification in the described processes, systems, or devices, and any further applications of the principles of the invention as described herein are contemplated as would normally occur to one skilled in the art to which the invention relates.

Instruments and techniques provide and facilitate implant re-positioning in and extraction from a space between vertebral bodies. The instruments can be provided in a kit to provide the surgeon with various options and capabilities during the procedure. The instruments and techniques can be employed in any approach to the space and with implants of any size and configuration. The implants can further be positioned in a spinal disc space between vertebrae or in a space provided by removal of all or a portion of one or more vertebral bodies in a corpectomy procedure. As used herein, the space between vertebrae is intended to encompass the space between adjacent vertebral bodies in intradiscal procedures and the space between vertebrae provided by removal of all or a portion of one or more vertebral bodies.

The instruments can include rotator instruments that can contact a wall of the implant to allow application of rotational and translational forces to re-position or re-orient the implant in the space between vertebrae. Hook instruments are also provided that allow a receptacle in the implant to be engaged with a hook member while the implant is in the space. The hook instrument can then be manipulated to remove or re-position the implant. Also provided are extractors with a proximal actuating structure and a distal implant engaging assembly operable by the proximal actuating structure to positively engage the implant. The implant engaging assembly can be pivotally or linearly movable to engage the implant in the space. Slap hammers, mallets, tuning instruments and other manipulators can be employed to facilitate application of re-positioning and removal forces adjacent the proximal ends of the instruments.

Referring to FIG. 1, there is shown a space S adjacent vertebral body V. Implant 50 is positioned in space S. In the illustrated embodiment, a postero-lateral approach A is shown, it being understood that other portal locations and approaches are contemplated. Implant 50 can be an intradiscal implant or a corpectomy device. Implant 50 can further include a banana or concavo-convex shape in plan view with the convex wall anteriorly oriented as shown, or any other suitable shape, including rectangular shapes, oval shapes, circular shapes, D-shapes, square shapes or irregular shapes. Implant 50 can be made from any suitable bio-compatible material, including bone material, metals and metal alloys, polymers, ceramics, carbon fiber, and combinations thereof.

A distal portion of a rotator instrument 100 is shown in FIG. 1 with a distal end member 102 contacting wall 52 of implant 50 adjacent a distal side D of the space S. As used herein, the proximal side P of space S is the side closest to the approach through which the instrument is positioned, and distal side D of the space S is opposite the proximal side P. Distal end member 102 includes a concave end wall 104 positionable in contact with implant 50 to allow application of re-positioning forces along a portion of the wall 52 of implant 50. An elongated shaft 106 extends proximally from end member 102 to allow remote manipulation of the implant 50, including contact with the side of implant 50 that is located or to be located opposite the approach A. For example, pushing forces directed along the longitudinal axis of the instrument as indicated by arrow 70 can be applied with rotator instrument 100 to rotate implant 50 into a desired orientation.

Simultaneously or alternately, pivoting or rotational forces can be applied as indicated by bi-directional arrow 72. The implant 50 can thus be pivoted and translated in the space to a desired position from an initial insertion position, or moved from an implanted position to facilitate access and removal of implant 50 by one or more other instruments.

In FIG. 2 there is shown a hook instrument 140 and implant 50 in sectional view.

Implant 50 includes a receptacle 54 in wall 52. Receptacle 54 can extend partially or completely through wall 52. Hook instrument 140 includes a shaft 142 and a distal hook member 144 at a distal end of shaft 142. Hook member 144 includes an arm 148 extending to a hooked end 146 that can be engaged in receptacle 54 to engage the implant and deliver forces to rotate or pivot it in space S, as indicated by bi-directional arrows 72, and alternately or simultaneously deliver forces that move implant 50 proximally in space S toward proximal side P as indicated by arrow 74.

In FIG. 2, hook member 144 includes arm 148 with a linear configuration extending to hooked end 146. In FIG. 3, another embodiment hook instrument 160 is shown with a hook member 164 including an angled configuration extending to a hooked end 166. Hook member 164 includes angled arm 168 including a first proximal section 170 extending from shaft 162 and a second distal section 172 angled relative to and extending distally from first proximal section 170 to hooked end 166. The angled arm 168 allows shaft 162 to be positioned at angles relative to implant 50 that differ than those provided by linear hook member 144.

Referring to FIG. 4, there is shown an extractor instrument 200 engaged to implant 50'. Implant 50' can be similar to implant 50 discussed above, and is shown in sectional view. Implant 50' includes wall 52' including a first receptacle 54' along one side thereof and a second receptacle 58' on or along a second side thereof. Receptacles 54', 58' can extend through or partially into wall 52', and can include any size or shape.

Extractor instrument 200 includes a shaft assembly 202 with a mounting assembly 204 and a rail assembly 240 movably mounted to mounting assembly 204. An engaging assembly 206 is provided at the distal end of shaft assembly 202 that is movable to clampingly engage implant 50'. Mounting assembly 204 includes a mounting member 208 and engaging assembly 206 includes a distal support member 210 extending distally from mounting member 208. Rail assembly 240 includes an elongated rail member 242 movable along mounting member 208 and engaging assembly 206 includes a distal clamping member 244 movably coupled to rail member 242. A linking portion 245 pivotally links clamping member 244 with one of support member 210 and mounting member 208. Longitudinal displacement of rail member 242 with a proximal actuating assembly (discussed further below) as indicated by bi-directional arrow 76 pivots clamping member 244 into and out of engagement with implant 50' as indicated by bi-directional arrow 78. Clamping member 244 works in conjunction with a flanged end 212 of support member 210 to clampingly engage implant 50' therebetween with flanged end 212 in receptacle 58' and clamping member 244 in receptacle 54'. With the implant 50' so engaged, implant 50' can be pivoted, rotated, translated and/or extracted from space S with extractor instrument 200.

Figure 5:
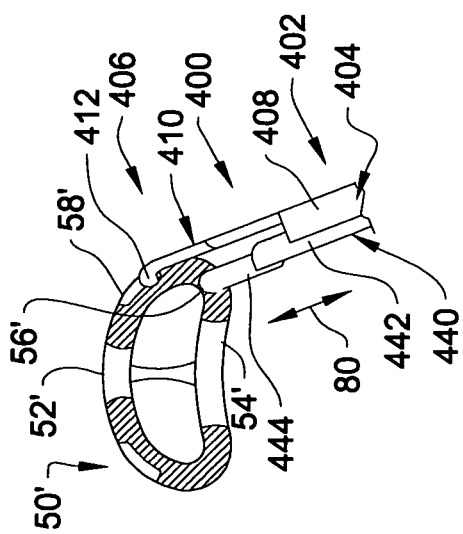
FIG. 5 is a plan view of an implant with another embodiment distal portion of an extractor instrument engaged thereto.

In FIG. 5, there is shown another embodiment extractor instrument 400 that includes a shaft assembly 402 with a mounting assembly 404 and a rail assembly 440 movably mounted to mounting assembly 404. An engaging assembly 406 is provided at the distal end of shaft assembly 402 that is longitudinally movable to clampingly engage implant 50'. Mounting assembly 404 includes a mounting member 408 and engaging assembly 406 includes a distal support member 410 extending distally from mounting member 408. Rail assembly 440 includes an elongated rail member 442 movable along mounting member 408 and engaging assembly 406 includes a distal clamping member 444 that moves longitudinally with rail member 442 as indicated by bi-direction arrow 80 with a proximal actuating assembly (discussed further below.) Clamping member 444 works in conjunction with a flanged end 412 of support member 410 to clampingly engage implant 50' therebetween with flanged end 412 in receptacle 58' and clamping member 444 axially received in a receptacle 56' in wall 52'. With the implant 50' so engaged, implant 50' can be pivoted, rotated, translated and/or extracted from space S with extractor instrument 400.

Referring now to FIGS. 6 and 7, further details of rotator instrument 100 will be discussed. Rotator instrument 100 includes elongated shaft 106 including a proximal handle 108 and distal end member 102 at a distal end of shaft 106 opposite handle 108. Distal end member 102 includes distally oriented end wall 104. Shaft 106 can include a distal shaft portion 112 extending along longitudinal axis 110 and a proximal shaft portion 114 offset from axis 110 with a pair of bends 116, 117 and an oblique shaft portion 118 extending obliquely to distal and proximal shaft portions 112, 114. The offset can facilitate viewing of distal end member 102 and the implant in contact therewith by positioning handle 108 out of the field of view. Handle 108 can be removably engaged to shaft 106 or formed integrally therewith. Embodiments with a non-offset shaft configuration are also contemplated.

In FIG. 7, distal end member 102 is shown and includes opposite feet 120, 122 extending in opposite directions from longitudinal axis 110. In the illustrated embodiment, first foot 120 extends outwardly a first width W1 and second foot 122 extends outwardly a second width W2. In one embodiment, width W1 is about 50% greater than width W2, although other arrangements are contemplated ranging from a difference of about 0% to a difference of about 100% or more. In addition, end member 102 includes feet 120, 122 that diverge distally from one another along an angle A1. Foot 120 extends along an angle A2 measured from longitudinal axis 110 that is less than the angle of foot 122 from longitudinal axis 110. In one embodiment, angle A1 is 90 degrees and angle A2 is 35 degrees. Other angular arrangements are also contemplated. The differing widths and angular relationships can facilitate pivoting movement of the implant by allowing the greater width foot 120 to pivot the implant toward the direction of shorter foot 122 without obstruction by the shorter foot 122.

End wall 104 can be concave and extend along an arc defined by a radius R. Radius R can be offset from axis 110 by a distance D1, although alignment of the center of radius R along axis 110 is also contemplated. Arc A can be provided with a shape to generally conform to a curvature of a wall portion of the implant to be contacted with end wall 104 to facilitate control of the implant and distribution of re-positioning forces over a larger surface area of the implant. Other embodiments contemplate other configurations for end wall 104, including a concave shape formed by linear and/or angular wall portions and implants with wall portions generally conforming in shape thereto.

FIG. 8 shows a tuning instrument 300 with a proximal handle 302, an intermediate shaft 304 and a distal instrument engaging structure 306. Engaging structure 306 includes a forked shape with a receptacle 308 between arms 310, 312 that can receive a shaft of an instrument. As discussed further below, arms 310, 312 can contact an adjustment member of the instrument to facilitate application of re-positioning and extraction forces to the instrument by manipulating tuning instrument 300, and thus tune or adjust the position of the implant in contact with the instrument.

In FIG. 9 there is shown hook instrument 140. Hook instrument 140 includes shaft 142 and hook member 144 at a distal end of shaft 142. Shaft 142 extends along longitudinal axis 143. Hook instrument 140 further includes a proximal handle 150 at a proximal end of shaft 142 and an adjustment member 152 extending outwardly from shaft 142 distally of handle 150. Adjustment member 152 can be contacted with an adjustment member, such as tuning instrument 300, at the proximal or distal sides thereof to facilitate application of adjustment forces to hook instrument 140 and thus to an implant engaged thereby.

Hook member 144 is shown in further detail in FIGS. 10 and 11. Hook member 144 includes a linear arm 148 extending and centered along longitudinal axis 143. Hook member 144 includes a proximal end member 154 that is engageable to shaft 142 by a press fit and epoxy or other suitable engagement structure or means, including fasteners, welding and the like. Hooked end 146 includes a first hook portion 146a transversely oriented to longitudinal axis 143 and linear arm 148, and a second hook portion 146b that extends from first hook portion 146a proximally and generally parallel to longitudinal axis 143. Hooked portion 146b is spaced from arm 148 to provide a space to engage the implant in hooked end 146. In one embodiment, first hook portion 146a includes a length L1 that is about 50% greater than a length L2 of second hook portion 146b. The lengths L1 and L2 can facilitate positioning of hooked end 146 in a receptacle and in engagement to the implant with the implant in space S while minimizing intrusion of hook instrument 140 into the adjacent tissue during engagement and disengagement with the implant. Other embodiments contemplate other relationships between the length of hook portions 146a, 146b, including lengths that are the same and lengths where hook portion 146b has a length greater than hook portion 146a.

As shown in FIG. 11, hooked end 146 can include a square-shaped cross-section to facilitate engagement with the implant in a manner that prevents or reduces rotation of the hooked end relative to the implant. Other embodiments contemplate other shapes for hooked end 146 and arm 148, including circular, rectangular, oval, polygonal, and non-circular shapes.

Referring now to FIG. 12, there is shown hook member 164, it being understood that hook instrument 160 could be provided with a shaft and handle structure like that discussed above for hook instrument 140. Hook member 164 includes angled arm 168 including proximal section 170 extending along longitudinal axis 163. Distal section 172 is angled relative to longitudinal axis 163 and proximal section 170 at an angle A2. In one embodiment, angle A2 is about 45 degrees, although other angular relationships are contemplated. The angular relationship facilitates positioning of the hook member 164 around a curved portion or bend of the implant body while minimizing intrusion of the hook member 164 into the adjacent tissue. Distal section 172 can have a length L3 extending to hooked end 166. Hooked end 166 includes a first portion 166a extending transversely to distal section 172 along a length L4 and a second portion 166b extending proximally from an end of first portion 166a along length L5 in a generally parallel and spaced relationship to distal section 172. In the illustrated embodiment, length L3 is greater than length L4 which is greater than length L5. Other arrangements contemplate other relationships between lengths L3, L4 and L5.

In FIGS. 13 and 14, there is shown extractor instrument 200 including shaft assembly 202 with mounting assembly 204 and rail assembly 240 mounted to mounting assembly 204. Engaging assembly 206 is provided at the distal end of shaft assembly 202 and is movable with an actuating assembly 270 to clampingly engage an implant.

Mounting assembly 204 includes mounting member 208 and rail assembly 240 includes an elongated rail member 242 movable along mounting member 208. Engaging assembly 206 includes distal support member 210 fixedly engaged to and extending distally from mounting member 208 and distal clamping member 244 movably coupled to rail member 242 with a first pin 298. Clamping member 244 includes a proximal linking portion 245 pivotally coupled with support member 210 with second pin 299. Longitudinal displacement of rail member 242 with proximal actuating assembly 270 translates pin 298 along clamping member 244 and pivots clamping member 244 about pin 299 into and out of engagement with the implant. Clamping member 244 works in conjunction with a flanged end 212 of support member 210 to clampingly engage the implant therebetween for re-positioning in and/or extraction of the implant from the space S with extractor instrument 200.

Mounting member 208 includes an elongated body extending between a distal end 214 and a proximal handle structure 216. An adjustment member 220 is provided extending proximally from handle structure 216 for engagement with an adjustment instrument, such as a slap hammer. An intermediate housing portion 218 is provided between handle structure 216 and mounting member 208. Housing portion 218 is configured for engagement with a trigger 272 of actuating assembly 270.

As shown in FIG. 19, trigger 272 includes a hand-hole portion 274 and an upper arm 276. Upper arm 276 includes a groove 278 and a central hole 280 extending therethrough. A locking hole 282 is provided between hand-hole portion 274 and central hole 280. Locking hole includes a through slot 282a and a recessed portion 282b extending about and off-center relative to slot 282a along one side of upper arm 276. Hand-hole portion 274 is sized to receive one or more fingers of the user's hand. Other arrangements for trigger 272 are also contemplated, such as where no hole is provided and one or more fingers of the user's hand extend around the trigger.

Referring now to FIG. 15, housing portion 218 includes a central slot 222 extending therethrough to receive arm 276 of trigger 272. Housing portion 218 further includes a first bore 224 to receive a mounting pin 290 (FIG. 14) through central hole 280 to pivotally couple trigger 272 to housing portion 218. In the illustrated embodiment, one side of bore 224 is threaded to threadingly engage mounting pin 290 while hole 280 is sized to allow rotation of trigger 272 about mounting pin 290. Housing portion 218 also includes a second bore 226 configured to receive a spring loaded locking pin 292, spring 294, and locking button 296. Locking button 292 includes a first portion 292a that is positioned in slot 282a in a manner that allows trigger 272 to be pivoted about mounting pin 290 to a position that engages the implant with engaging assembly 206. In this engaged position, a second, enlarged portion 292b of locking pin 292 is aligned with recess 282b, and spring 294 biases the enlarged portion 292b into recess 282b to lock trigger 272 and thus engaging assembly 206 to the implant. When it is desired to release the implant, button 296 can be pressed to force the enlarged portion 292b out of recess 282b and orient first portion 292a in slot 282a so that the trigger can move back along first portion 292a to the disengaged position.

Mounting member 208 further includes a proximal inverted T-shaped longitudinal slot 228 as shown in FIGS. 16 and 18 extending therealong and opening along an upper surface thereof proximally of central slot 222 to receive a proximal rail portion of rail member 242, as discussed further below. As shown in FIGS. 17 (with support member 210 removed) and 18, mounting member 208 includes a distal inverted T-shaped longitudinal slot 230 extending therealong adjacent distal end 214 to a distal rail portion of rail member 242, as discussed further below. Mounting member 208 also includes a bottom groove 232 adjacent distal end 214 that can receive support member 210, as discussed further below.

Referring now to FIGS. 20-21 there is shown rail member 242. Rail member 242 includes an elongated body extending between a distal mounting portion 246 and a proximal mounting portion 248. As shown further in FIG. 22, distal mounting portion 246 includes a pair of fingers 250 including holes 252 therethrough to receive mounting pin 298 to couple clamping member 244 to distal mounting portion 246. Second mounting pin 299 pivotally couples clamping member 244 to support member 210. As shown in FIG. 24, an inverted T-shaped rail portion 255 extends down from rail member 242 along distal mounting portion 246. Rail portion 255 is positionable in distal longitudinal slot 230 to secure rail member 242 along mounting member 208 while permitting longitudinal sliding movement therebetween. As shown in FIG. 25, proximal mounting portion 248 further includes a proximal T-shaped rail portion 262 that is slidably received in proximal longitudinal slot 228 of mounting member 208 while permitting longitudinal sliding movement therebetween.

Referring further to FIGS. 23 and 25, proximal mounting portion 248 will be further discussed. Proximal mounting portion 248 includes a body that increases in cross-sectional width and height to provide increased strength and stability along proximal mounting portion 248. Proximal mounting portion 248 includes an intermediate projection 256 extending therefrom that is received in a distal portion 223 (FIG. 18) of central slot 222 of housing portion 218. There is further provided a recessed area 258 including side holes 260 to receive a pin 261 (FIG. 13) that is positioned in groove 278 of trigger 272 (FIG. 19). Trigger 272 can pivot about pin 261 while upper arm 276 is movable in recessed area 258. Pin 261 assists in maintaining the desired orientation and positioning of trigger 272 relative to mounting portion 248. In addition, spring member 286 is positioned in distal portion 223 of central slot 222 and distally of intermediate projection 256. Spring member 286 contacts a distal end wall 225 (FIG. 18) of distal portion 223 and extends to a proximal end that contacts projection 256 to proximally bias rail member 242. Spring 286 also proximally biases upper arm 276 of trigger 272 about mounting pin 290 since trigger 272 is coupled to rail member 242 with pin 261. Spring 286 normally biases engaging assembly 206 to an open position. When trigger 272 is squeezed, rail member 242 is distally displaced against the bias of spring 286 by the upper arm 276 rotating about mounting pin 90 and displacing rail member 242 through its engagement thereto with the pin 261 in side holes 260.

Referring now to FIGS. 26 and 27, there is shown support member 210. Support member 210 includes a proximal tongue 320 configured for positioning in bottom groove 232 of mounting member 208 and securable therein with a press fit, epoxy, welding, fasteners and/or other suitable connecting arrangements. Support member 210 further includes a body portion 322 with a central slot 324 and side holes 326 to receive mounting pin 299 (FIG. 14). Body 322 includes a linear proximal section 323 and a distal section 325 angled relative to proximal section 323 toward clamping member 244. Support member 210 includes flange 212 at the distal end of distal section 325 that extends toward clamping member 244. Flange 212 forms a proximally oriented lip 213 that extends toward clamping member 244. The fixed relationship of support member 210 and angled body 322 facilitates placement of support member 210 into the space and around the implant without bending or pivoting of support member 210 so flange 212 can engage a receptacle in the implant.

In FIG. 28 there is shown clamping member 244 with proximal linking portion 245 including a through-hole 330 to receive mounting pin 299 and pivotally couple clamping member 244 in slot 324 of support member 210. Clamping member 244 includes an angled portion 336 extending from linking portion 245. Angled portion 336 includes an angled slot 332 through which pin 298 extends. Slot 332 includes a proximal end 332a and a distal end 332b that are both offset toward support member 210 when assembled thereto. Slot 332 defines an arcuate path angled away from support member 210 at a mid-portion thereof between ends 332a, 332b that is configured to provide positive seating of flange 334 with a receptacle or other structure of the implant. Clamping member 244 further includes an extension portion 338 that forms a concave recess 340 therealong oriented toward support member 210 to facilitate positioning of clamping arm 244 around the implant. Flange 334 is provided at the distal end of extension portion 338, and forms a proximally oriented lip 342 positionable in contact with the implant in conjunction with the proximally oriented lip formed by flange 212. The lips 213, 342 axially restrain the implant to engaging assembly 206 during re-positioning and extraction of the implant.

When assembled as shown in FIG. 13, trigger 272 is movable to longitudinally and distally displace upper rail member 242 of rail assembly 240 against the bias of spring 286. This movement in turn moves pin 298 along slot 332 of clamping member 244 from proximal end 332a toward distal end 332b. Clamping member 244 in turn pivots about its engagement with support member 210 so that flanged end 334 moves toward flanged end 212, clamping the implant therebetween with engaging assembly 206. The clamped engagement can be maintained by locking pin 292 positively engaging trigger 272 in the closed position. A slap hammer, tuning fork or other instrument can be engaged to adjustment member 220 to facilitate application of re-positioning and/or removal forces to move the implant in space S. When the implant has been re-positioned or removed, the trigger 272 can be unlocked by depressing button 296 to displace locking pin 292 relative to the trigger 272, and spring 286 biases rail member 242 proximally to pivot clamping member 244 away from support member 210 and release the implant from engaging assembly 206.

Referring to FIGS. 29-30, there is shown another embodiment extractor instrument 400 that is similar to extractor instrument 200, except that engaging assembly 406 does not include a pivoting arrangement but rather a longitudinal sliding arrangement. Trigger 472 is pivotally coupled with mounting assembly 402 with mounting pin 490 and linked to upper rail member 442 of rail assembly 440 with pin 443. Rail member 442 can be secured to and longitudinally movable along mounting member 408 with a rail and slot arrangement in a manner similar to that discussed above with respect to extractor instrument 200, except that there is no proximal spring bias of rail member 442, although such is not precluded. Mounting member 408 includes a support member 410 of engaging assembly 406 extending distally therefrom. Support member 410 can be configured like support member 210 discussed above, but does not include any slot to receive clamping member 444.

Upper rail member 442 includes clamping member 444 in the form of a cylinder with a rounded distal end formed by a bullet or ball-shaped tip that can be positioned in an implant receptacle. In use, support member 410 is positioned along one side of the implant with the hooked end in engagement with an implant receptacle. Trigger 472 is squeezed to distally and longitudinally displace rail member 442 and thus clamping member 444 toward the implant. When clamping member 444 is positioned in the implant receptacle, the implant is clamped between support member 410 and clamping member 444, and extraction or re-positioning of the implant can be performed with extractor instrument 400 as discussed above with respect to extractor instrument 200.

It is contemplated that the above-described instruments and methods can be used in substantially open surgical procedures. It is also contemplated that the instruments and methods may be utilized through guide sleeves or tubes. Sleeves and tubes can provide greater protection to adjacent tissues, reduce the size of access incisions, provide direct visualization of the surgical site, and/or provide enhanced control of the procedure. The instruments and methods may further be used in combination with disc space preparation and implant insertion through microscopic or endoscopic instruments that provide direct visualization of the surgical site.

The instruments discussed herein are suited for re-positioning and extracting an implant in a space between vertebrae for revision procedures. The rotator and hook instruments provide the surgeon the ability to re-position an implant in the space to a desired implantation orientation, or to re-position the implant for engagement with one of the extractor instruments. The rotator instruments can pivot and translate the implant in the disc space with a pushing force applied by manipulating the handle manually or with a mallet or other instrument. The hook instruments can re-position the implants by pivoting and pulling either manually or with supplemental instruments, such as with the tuning instrument. The extractor instruments can be employed to re-position the implants, or to remove the implants for another insertion attempt. The instruments can also be employed in revision procedures where a second surgical procedure is performed to access and re-position or remove the implant.

The re-positioning and extraction instruments can be provided in a kit, either separately or along with instruments for positioning the implants in the space between vertebrae. The kit can include a spinal implant with a wall defining a size and shape for positioning between vertebrae and at least one receptacle in the wall. The kit can also include a rotator instrument including a shaft extending along a longitudinal axis between a proximal handle and a distal end member that has a distal end wall with a shape to conform to a portion of the wall of the implant. The kit can also include a hook instrument that includes a shaft extending along a longitudinal axis between a proximal handle and a distal hook member configured to engage the implant in the at least one receptacle. The kit can further include an extractor instrument including a shaft assembly operably linking a proximal actuator assembly and a distal engaging assembly that is operable with the actuator assembly to clampingly engage the implant.

In one embodiment, the kit can also include a second hook instrument with a shaft extending along a longitudinal axis between a proximal handle and a distal hook member that is configured to engage the implant in the at least one receptacle. One of the hook members in the kit includes a linear arm extending from the shaft to a distal hooked end and the other of the hook members includes an angled arm extending from the shaft to a distal hooked end.

In another embodiment, the engaging assembly of the extractor instrument in the kit includes a clamping member movable with the actuator assembly and a support member fixed to the shaft assembly. In one form, the clamping member is movable longitudinally with the actuator assembly to clampingly engage said implant between said clamping member and said support member. In another form, the clamping member is pivotally movable with the actuator assembly to clampingly engage the implant between the clamping member and the support member.

In a further embodiment, the distal end wall of the rotator instrument in the kit includes a concave curvature extending transversely to the longitudinal axis.

In yet another embodiment, the kit can include a tuning instrument having a forked end. The hook instrument includes an adjustment member extending outwardly from the shaft, and the forked end is sized for positioning about the shaft of the hook instrument in contact with the adjustment member.

While the invention has been illustrated and described in detail in the drawings and the foregoing description, the same is considered to be illustrative and not restrictive in character. All changes and modifications that come within the spirit of the invention are desired to be protected.

What is claimed is:

1. A method for manipulating a spinal implant in a space between vertebrae, comprising:
    accessing a spinal implant positioned in the space between vertebrae through an opening into the space formed along a postero-lateral approach to the space, wherein the positioned spinal implant includes a wall with a first portion at a proximal side of the space closest to the opening and the wall of the positioned spinal implant includes a second portion at a distal side of the space opposite the proximal side;
    positioning a rotator through the opening to contact the second portion of the wall of the positioned spinal implant at the distal side of the space with a distal end of the rotator;
    moving the positioned spinal implant in the space to a desired orientation by pushing the second portion of the wall of the spinal implant at the distal side of the space with the distal end of the rotator;
    engaging the spinal implant with a hook member at a distal end of a hook instrument;
    pulling the spinal implant toward the opening into the space between the vertebrae;
    grasping the spinal implant with an engaging assembly of an extractor instrument; and
    removing the spinal implant from the space with the extractor instrument.

2. The method of claim 1, further comprising:
    pivoting the spinal implant in the space to the desired orientation in the space with the rotator.

3. The method of claim 1, wherein pulling the spinal implant includes pivoting the spinal implant with the hook instrument.

4. The method of claim 1, wherein engaging the spinal implant with the hook member includes positioning the hook member in a receptacle in a wall of the spinal implant.

5. The method of claim 4, wherein engaging the spinal implant with the hook member includes selecting between a first hook instrument with a hook member formed by a linear arm and a hooked end at a distal end of said linear arm and a second hook instrument with a hook member formed by an angled arm and a hooked end at a distal end of said angled arm.

6. The method of claim 1, wherein grasping the spinal implant with the engaging assembly includes positioning a support member of the engaging assembly in a receptacle of the spinal implant and linearly advancing a clamping member into a second receptacle of the spinal implant to clampingly engage the spinal implant between the support member and the clamping member.

7. The method of claim 1, wherein grasping the spinal implant with the engaging assembly includes positioning a support member of the engaging assembly in a receptacle of the spinal implant and pivotally advancing a clamping member toward the support member and into a second receptacle of the spinal implant to clampingly engage the spinal implant between the support member and the clamping member.

8. The method of claim 1, wherein the rotator includes an elongated shaft extending along a longitudinal axis, a handle at a proximal end of the shaft, and a distal end member at a distal end of the shaft, the distal end member including a distal end wall extending thereacross.

9. The method of claim 8, wherein the elongated shaft includes a proximal shaft portion offset from the longitudinal axis.

10. The method of claim 8, wherein the distal end member includes first and second feet that extend in opposite directions from one another away from the longitudinal axis.

11. The method of claim 10, wherein the first foot includes a first width extending outwardly from the longitudinal axis and the second foot includes a second width extending outwardly from the longitudinal axis, the first width being greater than the second width.

12. The method of claim 11, wherein the first and second feet diverge away from one another in a distal direction along the longitudinal axis.

13. The method of claim 12, wherein the distal end wall is concavely curved along an arc defined by a radius having a center offset from the longitudinal axis.

* * * * *